US00PP16683P2

(12) United States Plant Patent
Utecht

(10) Patent No.: US PP16,683 P2
(45) Date of Patent: Jun. 20, 2006

(54) *GERANIUM* PLANT NAMED 'FISMAXI'

(50) Latin Name: *Pelargonium peltatum*
Varietal Denomination: Fismaxi

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 90 days.

(21) Appl. No.: 10/998,559

(22) Filed: Nov. 30, 2004

(51) Int. Cl.
*A01H 5/00* (2006.01)

(52) U.S. Cl. ..... Plt./332
(58) Field of Classification Search ..... Plt./332
See application file for complete search history.

(56) References Cited

PUBLICATIONS

German PBR Application No. PEL 1895 filed Jun. 4, 2003 and withdrawn Oct. 5, 2004 (Copy of German Gazettes dated 1) Jul. 15, 2003—Listing Assigned Application for Protection No. (2 pgs), 2) May 15, 2004—Publishing Proposed Variety Denomination (2 pgs), and 3) Nov. 15, 2004—Listing Withdrawal of Application for Protection (2 pgs)).

Canadian PBR Application No. 03–3899 filed Nov. 21, 2003 (Copy of Canadian Plant Varieties Journal dated Jan., 2004 Listing Assigned Application No. (2 pgs).

Community Plant Variety Office (CPVO) No. 2004/1251 filed Jul. 5, 2004 (Copy of Official Gazette of the CPVO dated Oct. 15, 2004 Listing Assigned Application No. and Variety Denomination (3 pgs).

Fischer 2005 catalogue offering 'Fismaxi' (with shipment of plant material available starting Dec., 2004) (3 pgs).

*Primary Examiner*—Kent Bell
(74) *Attorney, Agent, or Firm*—Foley & Lardner LLP

(57) ABSTRACT

A new and distinct cultivar of *geranium* plant named 'Fismaxi', particularly characterized by the combined features of large, brilliant red, double-type flowers; numerous medium-sized, semi-spherically shaped inflorescences; deep green foliage with weak zonation, initially round and bushy, and later, somewhat trailing plant habit; and early spring flowering response.

1 Drawing Sheet

Genus and species of the plant claimed: *Pelargonium peltatum* L'Héritier (hybrid).
Variety denomination: 'Fismaxi'.

BACKGROUND OF THE INVENTION

The present invention comprises a new and distinct cultivar of *geranium*, botanically known as *Pelargonium peltatum*, and hereinafter referred to by the cultivar name 'Fismaxi'.

'Fismaxi' is a product of a planned breeding program which had the objective of creating new ivy *geranium* cultivars with semi-double to double flower type, zoned foliage, and about medium sized, well-branched growth habit, in various flower colors.

'Fismaxi' originated from a hybridization made by the inventor, Angelika Utecht, in a controlled breeding program in Hillscheid, Germany, in 2000.

The female parent was an unpatented hybrid plant, no. 97-2379-5, derived from a cross between the varieties 'Fiscoral' (U.S. Plant Pat. No. 12,995) and 'Fizzard' (U.S. Plant Pat. No. 10,992). The resulting seedling was characterized by orange-red flowers, deep green foliage, and about medium growth habit. The male parent of 'Fismaxi' was the unpatented plant No. 93-361-3, having deep red, semi-double flowers, large leaves with slight zonation, and long, trailing plant habit.

'Fismaxi' was selected as one flowering plant within the progeny of the stated cross by Angelika Utecht in 2001 in a controlled environment in Galdar, Gran Canaria, Spain.

The first act of asexual reproduction of 'Fismaxi' was accomplished when vegetative cuttings were taken from the initial selection in the fall of 2001, in a controlled environment in Galdar, Gran Canaria, Spain, by, or under the supervision of, Angelika Utecht.

Horticultural examination of plants grown from cuttings of the plant initiated in May of 2002 in Hillscheid, Germany, and continuing thereafter, has demonstrated that the combination of characteristics as herein disclosed for 'Fismaxi' are firmly fixed and are retained through successive generations of asexual reproduction.

BRIEF SUMMARY OF THE INVENTION

'Fismaxi' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fismaxi' in combination distinguish this *geranium* as a new and distinct cultivar:

1. large, brilliant red, double-type, flowers;
2. medium sized, semi-spherically shaped inflorescences;
3. deep green foliage with weak zonation;

4. medium growth habit, and very well-branched, round plant habit; and
5. early spring flowering response and rich flowering.

Of the many commercial cultivars known to the present inventor, the most similar ones are the patented varieties 'Fip 101' (U.S. Plant Pat. No. 14,008) and 'Fisbeach' (U.S. Plant Pat. No. 12,408).

In comparison to 'Fip 101', 'Fismaxi' has a slightly more scarlet or orange-red hue of flower color, larger inflorescences, even weaker zonation on foliage, and taller plant habit. In comparison to 'Fisbeach', inflorescences of 'Fismaxi' appear relatively close, but its growth habit is much less vigorous, and the diameter of plants measures roughly half the size by the end of summer. Furthermore, 'Fismaxi' develops at least weak zonation on leaves, and beginning of flowering is earlier.

BRIEF DESCRIPTION OF THE DRAWINGS

The accompanying photographic drawing shows typical flower and foliage characteristics of 'Fismaxi' with colors being as true as possible with an illustration of this type.

The photographic drawing shows as FIG. 1 a close-up view of a branch end of 'Fismaxi' with leaves, buds and inflorescences; and as FIG. 2 a side perspective view of a flowering hanging basket of 'Fismaxi' with leaves, buds and inflorescences.

DETAILED BOTANICAL DESCRIPTION

The measurements were taken in Hillscheid, Germany, in mid May 2003, 15 weeks after planting of rooted cuttings. The plants were growing in 14 cm pots; they had been pinched once.

In the following description color references are made to The Royal Horticultural Society Color Chart. The color values were determined indoors from plants growing in a green-house in May 2003, in Hillscheid, Germany.

Parentage:

*Male parent.*—Unpatented, hybrid plant no. 93-361-3.

*Female parent.*—Unpatented, hybrid plant no. 97-2379-5.

Classification: *Pelargonium peltatum* L'Héritier (hybrid).

Propagation: Vegetative cuttings.

Inflorescence:

*Umbel.*—Shape: Semi-spherical. Average diameter: 81 mm. Average depth: 55–60 mm.

*Peduncle.*—Peduncle length: 147 mm. Peduncle diameter: 2–3 mm. Peduncle color: Light green, RHS 144 A.

*Pedicel.*—Pedicel length: 28 mm in length, usually no spur visible. Pedicel diameter: 1.5 mm. Pedicel color: Green, RHS 141 C, partly greyed-red, RHS 179 B. Number of flowers per umbel: About 8–12.

*Corolla.*—Average length: 57 mm. Average width: 54 mm. Depth: 15 mm. Form: Double-type. Shape: Oval outline, with the upper petals longer than the lower petals.

*Petaloids.*—Number of petaloids. 2–5. Length: 8 mm. Width: Often 2 mm, occasionally often 2 mm, up to occasionally 6 mm. Overall shape: Variable, often threadlike (filiform). Apex shape: Rounded. Base shape: Mostly attenuate. Margin: Entire. Color of upper petaloids: Red, RHS 44 A. Color of lower petaloids: Red, RHS 44 A.

*Petals.*—Number of petals: 12–15. Shape of petals: Obovate, base acute or attenuate, upper end is rounded, margin is entire. Size of petals: Upper petals: 33 mm long, 16 mm wide. Lower petals: 26 mm long, 16–17 mm wide. Color (general tonality from a distance of three meters): Brilliant red, uniform. Color of upper petals: Red, RHS 44 A. Markings of upper petals: 2 blackish veins, greyed-purple, RHS 187 A. Color of lower petals: Red, RHS 44 A. Markings of lower petals: None. Color of lower surface of petals: Red, approximately RHS 45 C.

*Sepals.*—Number of sepals: 5. Shape of sepals: Linear to lanceolate, acute tip, fused base, surface with weak pubescence, margin entire. Size of sepals: 14 mm long, 5 mm wide for the largest upper sepal, 2–3 mm in width for the other sepals. Color of sepals: Outer, lower, visible lower surface: light green, RHS 143 C; the largest sepal may be brownish infused (greyed-red); RHS 179 B inner, upper, surface: light green, RHS 144 A.

*Bud: (just prior to petals unfolding).*—Shape: Elliptical. Color of sepals: Light green, RHS 143 B. Color of petals: Red, RHS 44A. Length: 23 mm. Width: 13 mm.

Reproductive organs:

*Androecium.*—7 or more fertile anthers, moderate pollen, orange, RHS N25A, lower side of anthers grey-purple, RHS 187 A, filaments white, RHS 155 D, to light pink, RHS 55 B.

*Gynoecium.*—One pistil, whitish style, RHS 155 D to red-purple, RHS 65 D, stigma 5–6-lobed stigma, dark red, RHS 46 A.

*Fertility/seed set.*—Few, mainly from late summer to fall.

*Fruit.*—Oblong, about 5–6 mm wide, rostrum (beak) 38–42 mm long.

*Seed.*—Oblong, 4–5 mm long, brown (greyed-orange), RHS 177 B.

*Spring flowering response period.*—In Hillscheid, Germany, in 2003 plants had on average 1.5 flowers opened 12 weeks after planting of rooted cuttings (pinched plants).

*Outdoor flower production.*—Continuously and rich flowering, the flower count in 2003 in Hillscheid, Germany, indicated about 25–33 inflorescence per plant in late summer.

*Durability.*—Good stability of flower color, may occasionally fade somewhat, fair resistance against "shattering" (dropping of petals).

*Lastingness of the individual flower.*—About 8 days at 18° C.

*Fragrance.*—None.

Plant:

*Foliage.*—Overall Shape: Ivy-shaped. Base Shape: Cordate base, with the gap between the lowest lobes slightly open to closed. Apex Shape: Apex rounded with distinct lobes. Margin: Most often somewhat crenate, or with single notches, slightly wavy. Texture: Upper surface smooth, slightly glossy. Size of leaf: 89 mm wide, about 55 mm in length. Color of upper surface: Medium green, closest to RHS 137 B. Color of zonation: Brown (greyed-orange), near RHS 166 A, distinctness: weak. Color of lower surface: Green, RHS 143 C. Petiole: 35–50 mm long, 2–3 mm diameter, light green in color, closest to RHS 143 B.

*General appearance and form.*—Stem color: Length green, RHS 143 B. Internode length: 50–70 mm.

Branching pattern: 9.3 branches on average. Size of plants: (branches initially ascending, later overhanging and somewhat trailing). Height: 21.5 cm (15 week-old plants, as described). Diameter: 26 cm (15 week-old plants, as described). Length: 26 cm (15 week-old plants, as described), and 71 cm (30 week-old plants, around September 1), measured from the top of the soil (base of the main stem) to the tips of the branches, without inflorescences.

I claim:

1. A new and distinct cultivar of *geranium* plant named 'Fismaxi', as described and illustrated herein.

* * * * *

FIG. 1
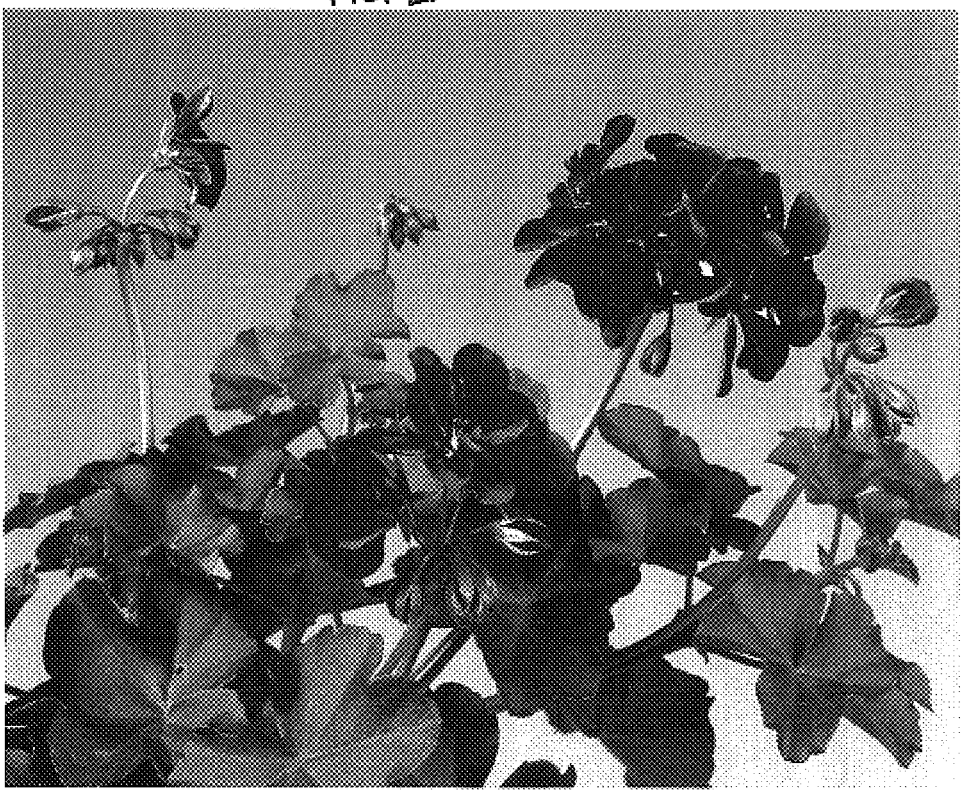
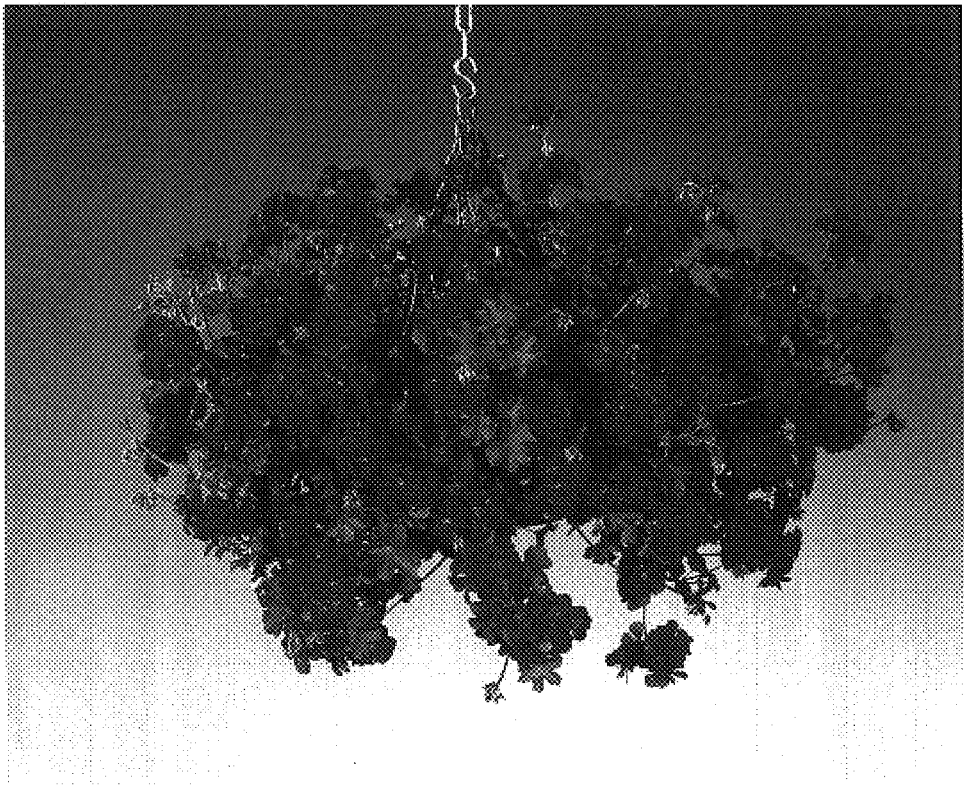
FIG. 2